US012742031B2

(12) United States Patent
Nadano et al.

(10) Patent No.: US 12,742,031 B2
(45) Date of Patent: Sep. 22, 2026

(54) METHOD FOR PRODUCING FLUORINE-CONTAINING POLYMER AND COMPOSITION

(71) Applicant: Central Glass Company, Limited, Ube (JP)

(72) Inventors: Ryo Nadano, Tokyo (JP); Satoru Miyazawa, Tokyo (JP); Yuzuru Kaneko, Saitama (JP)

(73) Assignee: Central Glass Company, Limited, Ube (JP)

( * ) Notice: Subject to any disclaimer, the term of this patent is extended or adjusted under 35 U.S.C. 154(b) by 596 days.

(21) Appl. No.: 18/266,329

(22) PCT Filed: Dec. 2, 2021

(86) PCT No.: PCT/JP2021/044211

§ 371 (c)(1),
(2) Date: Jun. 9, 2023

(87) PCT Pub. No.: WO2022/124182

PCT Pub. Date: Jun. 16, 2022

(65) Prior Publication Data

US 2024/0124632 A1 Apr. 18, 2024

(30) Foreign Application Priority Data

Dec. 10, 2020 (JP) ................................ 2020-205257

(51) Int. Cl.

| | |
|---|---|
| ***C07F 11/00*** | (2006.01) |
| ***C07C 67/08*** | (2006.01) |
| ***C07C 67/54*** | (2006.01) |
| ***C07C 69/653*** | (2006.01) |
| ***C08F 220/24*** | (2006.01) |

(52) U.S. Cl.

CPC ............ *C08F 220/24* (2013.01); *C07C 67/08* (2013.01); *C07C 67/54* (2013.01); *C07C 69/653* (2013.01)

(58) Field of Classification Search

None

See application file for complete search history.

(56) References Cited

U.S. PATENT DOCUMENTS

| | | | |
|---|---|---|---|
| 2003/0078352 A1 | 4/2003 | Miyazawa et al. | |
| 2004/0236046 A1 | 11/2004 | Miyazawa et al. | |
| 2006/0217507 A1 | 9/2006 | Miyazawa et al. | |
| 2006/0252897 A1 | 11/2006 | Miyazawa et al. | |
| 2020/0089116 A1 | 3/2020 | Kaneko et al. | |
| 2021/0317065 A1* | 10/2021 | Miyazawa ............ | C08F 120/24 |

FOREIGN PATENT DOCUMENTS

| | | | | |
|---|---|---|---|---|
| CN | 1819987 A | 8/2006 | | |
| CN | 110730790 A | 1/2020 | | |
| JP | 4083399 B2 | 4/2008 | | |
| JP | 2010-1273 A | 1/2010 | | |
| JP | 6489275 B1 * | 3/2019 | ............. | C07C 67/62 |
| JP | 2020-26410 A | 2/2020 | | |

OTHER PUBLICATIONS

JP 2010-001273 machine translation. (Year: 2010).*

International Search Report (PCT/ISA/210) issued in PCT Application No. PCT/JP2021/044211 dated Dec. 28, 2021 with English translation (4 pages).

Japanese-language Written Opinion (PCT/ISA/237) issued in PCT Application No. PCT/JP2021/044211 dated Dec. 28, 2021 (3 pages).

* cited by examiner

*Primary Examiner* — Catherine S Branch

(74) *Attorney, Agent, or Firm* — Crowell & Moring LLP

(57) ABSTRACT

Provided is a method for producing a fluorine-containing polymer with little lot-to-lot variation in weight average molecular weight. The method for producing a fluorine-containing polymer of the present invention relates to a method for producing a fluorine-containing polymer containing a repeating unit of formula (1) and a repeating unit of formula (2), which includes: fluorine-containing monomer synthesis including reacting a diol of formula (3) with at least one selected from the group consisting of unsaturated carboxylic acids, esters of the unsaturated carboxylic acids, acid halides of the unsaturated carboxylic acids, and anhydrides of the unsaturated carboxylic acids, to obtain a composition containing a fluorine-containing monomer of formula (4) as a main reaction product and a fluorine-containing monomer of formula (5) as a minor reaction product; fluorine-containing monomer purification including removing the fluorine-containing monomer of formula (5) from the composition to adjust the amount of the fluorine-containing monomer of formula (5), expressed in parts per million based on the mass of the fluorine-containing monomer of formula (4), to 1500 ppm or less; and polymerization including performing a polymerization reaction of the composition obtained after the fluorine-containing monomer purification to give the fluorine-containing polymer containing the repeating unit of formula (1) and the repeating unit of formula (2).

17 Claims, No Drawings

METHOD FOR PRODUCING FLUORINE-CONTAINING POLYMER AND COMPOSITION

TECHNICAL FIELD

The present disclosure relates to a method for producing a fluorine-containing polymer, and a composition.

BACKGROUND ART

Fluorine-containing polymers (fluorine-containing compounds) have continued to be used or developed in a wide range of application fields, mainly in the field of advanced materials, due to the properties of fluorine, such as water repellency, oil repellency, low water absorption, heat resistance, weather resistance, corrosion resistance, transparency, photosensitivity, low refractive index, and low dielectric properties. In particular, when it comes to coating applications, active research and development have been conducted in the fields of antireflection films using low refractive index and transparency of visible light, optical devices using transparency in the high wavelength range (optical communication wavelength band), resist materials using transparency in the ultraviolet region (especially in the vacuum ultraviolet wavelength range), etc. The common polymer design in these application fields is to achieve adhesion to the substrate and a high glass transition temperature (hardness) while achieving transparency at the respective operating wavelengths by introducing as many fluorine atoms as possible.

Patent Literature 1 describes as a monomer constituting such a fluorine-containing polymer a polymerizable monomer represented by the following formula (6):

[Chem. 1]

(6)

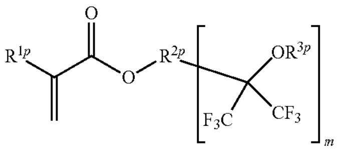

wherein $R^{1p}$ represents a hydrogen atom, a halogen atom, or a group selected from the group consisting of a hydrocarbon group and a fluorine-containing alkyl group which is linear or branched and optionally contains a cyclic structure; $R^{2p}$ is a divalent or trivalent organic group selected from an aliphatic hydrocarbon group which is linear or branched and optionally contains a cyclic structure, an aromatic ring group, or a complex substituent thereof, with a part or all of the hydrogen atoms in the organic group being optionally replaced by a fluorine atom or a hydroxy group; $R^{3p}$ is a hydrogen atom, a hydrocarbon group, a fluorine-containing alkyl group which is linear or branched and optionally contains a cyclic structure, or an aromatic ring group, the hydrocarbon group or fluorine-containing alkyl group optionally internally containing a divalent linking group selected from an ether group (—O—) or a carbonyl group (—(C═O)—); and m represents an integer of 1 or 2, and when m is 2, two $R^{3p}$ may be the same as or different from each other.

The polymerizable monomer of formula (6) is a monomer compound successfully produced to contain a $(CF_3)_2(OR^{3p})C$— moiety derived from hexafluoroacetone and have a high fluorine content while bearing polar groups in the same molecule in a balanced way.

The polymerizable monomer is also excellent in polymerizability. The fluorine-containing polymer obtained by polymerizing the polymerizable monomer is known to combine transparency brought about by the fluorine atoms with adhesion and workability brought about by the polar groups, and show excellent physical properties as antireflection film materials, optical device materials, resist materials, or other materials.

CITATION LIST

Patent Literature

Patent Literature 1: JP 4083399 B

SUMMARY OF INVENTION

Technical Problem

There has been a phenomenon where when a fluorine-containing polymer is produced from the polymerizable monomer of formula (6) in which $R^{3p}$ is hydrogen, that is, the polymerizable monomer of formula (6) having a hydroxy group, the weight average molecular weight of the fluorine-containing polymer varies from lot to lot.

When the fluorine-containing polymer whose weight average molecular weight varies from lot to lot is used to form resist patterns, the alkali solubility of the polymer may vary and the exposure and development conditions for forming resist patterns may need to be adjusted from lot to lot, which may affect semiconductor production efficiency.

The present disclosure aims to provide a method for producing a fluorine-containing polymer with little lot-to-lot variation in weight average molecular weight.

Solution to Problem

In view of the above problem, the present inventors conducted extensive studies. As a result, the present inventors have found that the minor reaction product generated during the production of the polymerizable monomer causes lot-to-lot variation in the weight average molecular weight of the fluorine-containing polymer. This finding has led to the present disclosure.

Specifically, the present disclosure is as follows.

The method for producing a fluorine-containing polymer of the present disclosure relates to a method for producing a fluorine-containing polymer containing a repeating unit represented by the following formula (1) and a repeating unit represented by the following formula (2), the method including:

- fluorine-containing monomer synthesis including reacting a diol represented by the following formula (3) with at least one selected from the group consisting of unsaturated carboxylic acids, esters of the unsaturated carboxylic acids, acid halides of the unsaturated carboxylic acids, and anhydrides of the unsaturated carboxylic acids, to obtain a composition containing a fluorine-containing monomer represented by the following formula (4) as a main reaction product and a fluorine-containing monomer represented by the following formula (5) as a minor reaction product;
- fluorine-containing monomer purification including removing the fluorine-containing monomer of formula (5) from the composition to adjust an amount of the fluorine-containing monomer of formula (5), expressed in parts per million based on a mass of the fluorine-containing monomer of formula (4), to 1500 ppm or less; and polymerization including performing a polymerization reaction of the composition obtained after the fluorine-containing monomer purification to give the fluorine-containing polymer containing the repeating unit of formula (1) and the repeating unit of formula (2),

[Chem. 2]

(1)

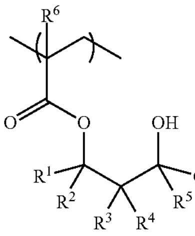

(2)

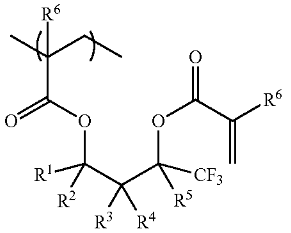

(3)

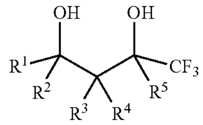

(4)

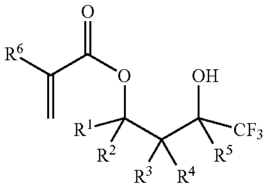

(5)

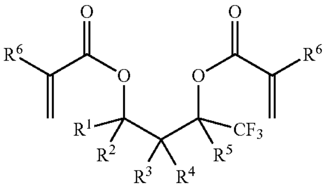

wherein $R^1$ and $R^2$ are each independently a hydrogen atom, a methyl group, an ethyl group, an n-propyl group, an iso-propyl group, an n-butyl group, an iso-butyl group, a sec-butyl group, or a t-butyl group; $R^3$ and $R^4$ are each independently a hydrogen atom, a methyl group, or an ethyl group; $R^5$ is a hydrogen atom or a trifluoromethyl group; and $R^6$ is a hydrogen atom, a chlorine atom, a methyl group, or a trifluoromethyl group.

Preferably, in the polymerization in the method for producing a fluorine-containing polymer of the present disclosure, the fluorine-containing polymer is synthesized such that a relative standard deviation, which is a numerical value obtained by dividing a standard deviation of a weight average molecular weight of the fluorine-containing polymer to be obtained by an average weight average molecular weight of the fluorine-containing polymer, is 0.10 to 1.10.

Preferably, in the method for producing a fluorine-containing polymer of the present disclosure, $R^5$ is a trifluoromethyl group.

Preferably, in the method for producing a fluorine-containing polymer of the present disclosure, $R^3$ and $R^4$ are hydrogen atoms.

Preferably, in the method for producing a fluorine-containing polymer of the present disclosure, $R^1$ is a methyl group or an iso-propyl group, and $R^2$ is a hydrogen atom.

Preferably, in the method for producing a fluorine-containing polymer of the present disclosure, the polymerization includes performing the polymerization reaction of the composition containing another monomer other than the fluorine-containing monomer of formula (4) and the fluorine-containing monomer of formula (5).

Preferably, in the method for producing a fluorine-containing polymer of the present disclosure, the polymerization reaction in the polymerization is a radical polymerization reaction.

Preferably, in the method for producing a fluorine-containing polymer of the present disclosure, the radical polymerization reaction is performed in an organic solvent.

A composition according to the present disclosure contains a fluorine-containing monomer represented by the following formula (4), and a fluorine-containing monomer represented by the following formula (5) in an amount, expressed in parts per million based on a mass of the fluorine-containing monomer of formula (4), of 1500 ppm or less,

[Chem. 3]

(4)

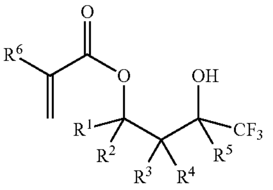

(5)

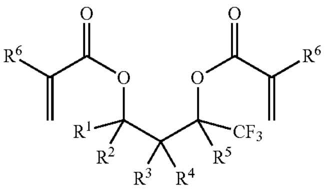

wherein $R^1$ and $R^2$ are each independently a hydrogen atom, a methyl group, an ethyl group, an n-propyl group, an iso-propyl group, an n-butyl group, an iso-butyl group, a sec-butyl group, or a t-butyl group; $R^3$ and $R^4$ are each independently a hydrogen atom, a methyl group, or an ethyl group; $R^5$ is a hydrogen atom or a trifluoromethyl group; and $R^6$ is a hydrogen atom, a chlorine atom, a methyl group, or a trifluoromethyl group.

Preferably, in the composition of the present disclosure, $R^5$ is a trifluoromethyl group.

Preferably, in the composition of the present disclosure, $R^3$ and $R^4$ are hydrogen atoms.

Preferably, in the composition of the present disclosure, $R^1$ is a methyl group or an iso-propyl group, and $R^2$ is a hydrogen atom.

Preferably, the composition of the present disclosure further contains another monomer other than the fluorine-containing monomer of formula (4) and the fluorine-containing monomer of formula (5).

Preferably, the composition of the present disclosure further contains an organic solvent.

Advantageous Effects of Invention

The present disclosure can provide a method for producing a fluorine-containing polymer with little lot-to-lot variation in weight average molecular weight.

Moreover, as the composition of the present disclosure contains only a small amount of the fluorine-containing monomer of formula (5), the composition of the present disclosure can be used to produce a fluorine-containing polymer with little lot-to-lot variation in weight average molecular weight.

DESCRIPTION OF EMBODIMENTS

The present disclosure is described in detail below, but the description of the constituent elements described below relates to exemplary embodiments of the present disclosure, and the present disclosure is not limited to these specific contents. The present disclosure can be carried out in various modifications within the scope of the gist.

In the section "DESCRIPTION OF EMBODIMENTS" herein, the matters denoted by the brackets "[" and "]" and "<" and ">" are merely symbols and have no meaning per se.

The method for producing a fluorine-containing polymer of the present disclosure relates to a method for producing a fluorine-containing polymer containing a repeating unit represented by the following formula (1) and a repeating unit represented by the following formula (2), which includes a fluorine-containing monomer synthesis step, a fluorine-containing monomer purification step, and a polymerization step.

The fluorine-containing monomer synthesis step includes reacting a diol represented by the following formula (3) with at least one selected from the group consisting of unsaturated carboxylic acids, esters of the unsaturated carboxylic acids, acid halides of the unsaturated carboxylic acids, and anhydrides of the unsaturated carboxylic acids, to obtain a composition containing a fluorine-containing monomer represented by the following formula (4) as a main reaction product and a fluorine-containing monomer represented by the following formula (5) as a minor reaction product.

The fluorine-containing monomer purification step includes removing the fluorine-containing monomer of formula (5) from the composition obtained in the fluorine-containing monomer synthesis step to adjust the amount of the fluorine-containing monomer of formula (5), expressed in parts per million based on the mass of the fluorine-containing monomer of formula (4), to 1500 ppm or less.

The polymerization step includes performing a polymerization reaction of the composition obtained after the fluorine-containing monomer purification step to give the fluorine-containing polymer containing the repeating unit of formula (1) and the repeating unit of formula (2).

[Chem. 4]

(1)

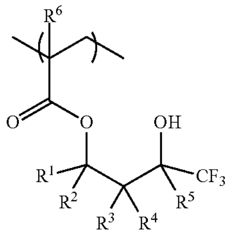

(2)

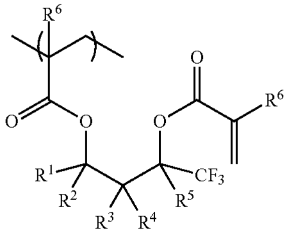

(3)

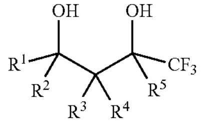

(4)

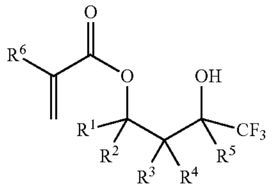

(5)

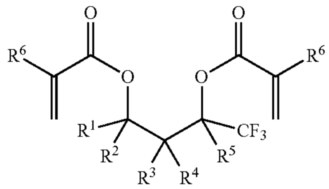

In the formulas (1), (2), (3), (4), and (5), $R^2$ and $R^2$ are each independently a hydrogen atom, a methyl group, an ethyl group, an n-propyl group, an iso-propyl group, an n-butyl group, an iso-butyl group, a sec-butyl group, or a t-butyl group; $R^3$ and $R^4$ are each independently a hydrogen atom, a methyl group, or an ethyl group; $R^5$ is a hydrogen atom or a trifluoromethyl group; and $R^6$ is a hydrogen atom, a chlorine atom, a methyl group, or a trifluoromethyl group.

In the fluorine-containing monomer synthesis step in the method for producing a fluorine-containing polymer of the present disclosure, the fluorine-containing monomer of formula (4) as a main reaction product and the fluorine-containing monomer of formula (5) as a minor reaction product are produced. The fluorine-containing monomer of formula (5) as a minor reaction product can cause lot-to-lot variation in the weight average molecular weight of the fluorine-containing polymer to be obtained through the subsequent steps.

However, the fluorine-containing monomer purification step in the method for producing a fluorine-containing polymer of the present disclosure includes removing the fluorine-containing monomer of formula (5) as a minor reaction product from the composition to adjust the amount of the fluorine-containing monomer of formula (5), expressed in parts per million based on the mass of the fluorine-containing monomer of formula (4), to 1500 ppm or less. Thus, the method for producing a fluorine-containing polymer of the present disclosure can produce a fluorine-containing polymer with little lot-to-lot variation in the weight average molecular weight of the fluorine-containing polymer.

The following specifically describes the steps in the method for producing a fluorine-containing polymer of the present disclosure.

Fluorine-Containing Monomer Synthesis Step

In the method for producing a fluorine-containing polymer of the present disclosure, first, a fluorine-containing monomer synthesis step is performed.

The fluorine-containing monomer synthesis step includes reacting a diol represented by the following formula (3) with at least one selected from the group consisting of unsaturated carboxylic acids, esters of the unsaturated carboxylic acids, acid halides of the unsaturated carboxylic acids, and anhydrides of the unsaturated carboxylic acids (hereinafter also referred to as "any of the unsaturated carboxylic acids and the like").

Thus, a composition containing a fluorine-containing monomer represented by the following formula (4) as a main reaction product and a fluorine-containing monomer represented by the following formula (5) as a minor reaction product can be obtained.

[Chem. 5]

(3)

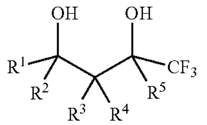

(4)

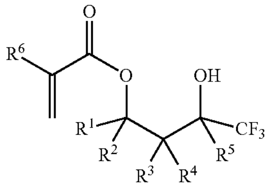

(5)

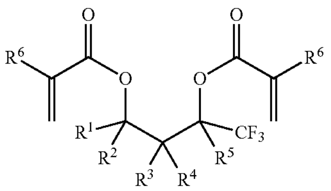

In the formulas (3), (4), and (5), $R^1$ and $R^2$ are each independently a hydrogen atom, a methyl group, an ethyl group, an n-propyl group, an iso-propyl group, an n-butyl group, an iso-butyl group, a sec-butyl group, or a t-butyl group; $R^3$ and $R^4$ are each independently a hydrogen atom, a methyl group, or an ethyl group; $R^5$ is a hydrogen atom or a trifluoromethyl group; and $R^6$ is a hydrogen atom, a chlorine atom, a methyl group, or a trifluoromethyl group.

In the reaction in the fluorine-containing monomer synthesis step, the diol of formula (3) has two alcohol moieties, a fluorine-containing alcohol moiety containing a fluorine atom and an alkyl alcohol moiety containing no fluorine atom, in the same molecule. The fluorine-containing alcohol moiety contains a bulky trifluoromethyl group having electron-withdrawing properties.

It is believed that, owing to the electron-withdrawing properties of the fluorine-containing alcohol moiety and its steric effect, the nucleophilicity of the lone pair of electrons in the alcohol moiety may be reduced, so that an addition reaction of any of the unsaturated carboxylic acids and the like is less likely to occur. Thus, the fluorine-containing monomer of formula (4) can be synthesized as a main reaction product.

Moreover, the fluorine-containing monomer of formula (4) contains a residual fluorine-containing alcohol moiety. At this fluorine-containing alcohol moiety, an addition reaction of any of the unsaturated carboxylic acids and the like can slightly occur. Thus, in the synthesis of the fluorine-containing monomer of formula (4), the fluorine-containing monomer of formula (5) as an unavoidable minor reaction product will be synthesized.

As a result, the composition obtained in the fluorine-containing monomer synthesis step contains the fluorine-containing monomer of formula (4) as a main reaction product and the fluorine-containing monomer of formula (5) as a minor reaction product.

Moreover, in the fluorine-containing monomer synthesis step, any of the unsaturated carboxylic acids and the like may be further added to the site where any of the unsaturated carboxylic acids and the like is added in the fluorine-containing monomer of formula (4), to synthesize a fluorine-containing monomer represented by the following formula (7).

The composition obtained in the fluorine-containing monomer synthesis step may contain the fluorine-containing monomer of formula (7):

[Chem. 6]

(7)

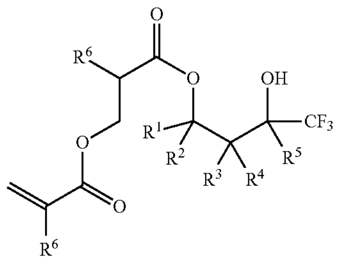

wherein $R^2$ and $R^2$ are each independently a hydrogen atom, a methyl group, an ethyl group, an n-propyl group, an iso-propyl group, an n-butyl group, an iso-butyl group, a sec-butyl group, or a t-butyl group; $R^3$ and $R^4$ are each independently a hydrogen atom, a methyl group, or an ethyl group; $R^5$ is a hydrogen atom or a trifluoromethyl group; and $R^6$ is a hydrogen atom, a chlorine atom, a methyl group, or a trifluoromethyl group.

As described above, the fluorine-containing alcohol moiety containing a fluorine atom in the diol of formula (3) is less likely to undergo an addition reaction of any of the unsaturated carboxylic acids and the like. Thus, compounds in which only the fluorine-containing alcohol moiety containing a fluorine atom has undergone an addition reaction of any of the unsaturated carboxylic acids and the like are hardly produced. Moreover, even if such a compound is produced, the highly reactive alkyl alcohol moiety containing no fluorine atom will immediately undergo an addition reaction of any of the unsaturated carboxylic acids and the like to synthesize the fluorine-containing monomer of formula (5).

Thus, compounds in which only the fluorine-containing alcohol moiety containing a fluorine atom in the diol of formula (3) has undergone an addition reaction of any of the unsaturated carboxylic acids and the like are hardly detected in the composition obtained in the fluorine-containing monomer synthesis step in the present disclosure.

From the standpoint of easy availability, in the diol of formula (3), $R^1$ is preferably a methyl group or an iso-propyl group, $R^2$ to $R^4$ are preferably hydrogen atoms, and $R^5$ is preferably a trifluoromethyl group.

Examples of the at least one selected from the group consisting of unsaturated carboxylic acids, esters of the unsaturated carboxylic acids, acid halides of the unsaturated carboxylic acids, and anhydrides of the unsaturated carboxylic acids used in the fluorine-containing monomer synthesis step include methacrylating agents, acrylating agents, and other esterifying agents.

Examples of methacrylating agents that may be used in the fluorine-containing monomer synthesis step include methacrylic acid esters such as methyl methacrylate, ethyl methacrylate, n-propyl methacrylate, iso-propyl methacrylate, n-butyl methacrylate, iso-butyl methacrylate, sec-butyl methacrylate, and tert-butyl methacrylate; acid halides such as methacrylic acid chloride, methacrylic acid fluoride, and methacrylic acid bromide; methacrylic anhydride; and methacrylic acid.

Examples of acrylating agents that may be used in the fluorine-containing monomer synthesis step include acrylic acid esters such as methyl acrylate, ethyl acrylate, n-propyl acrylate, iso-propyl acrylate, n-butyl acrylate, iso-butyl acrylate, sec-butyl acrylate, and tert-butyl acrylate; acid halides such as acrylic acid chloride, acrylic acid fluoride, and acrylic acid bromide; acrylic anhydride; and acrylic acid.

Examples of other esterifying agents that may be used in the fluorine-containing monomer synthesis step include carboxylic acid esters, acid halides such as carboxylic acid chlorides, carboxylic acid anhydrides, and carboxylic acids, which do not fall into the above-mentioned methacrylating agents and acrylating agents.

Methacrylating agents are preferred among these, with methacrylic anhydride and/or methacrylic acid chloride being more preferred.

In the fluorine-containing monomer synthesis step, when the diol of formula (3) is reacted with at least one selected from the group consisting of unsaturated carboxylic acids, esters of the unsaturated carboxylic acids, acid halides of the unsaturated carboxylic acids, and anhydrides of the unsaturated carboxylic acids, an acid or a base may be added as needed.

In the fluorine-containing monomer synthesis step, when the diol of formula (3) is reacted with at least one selected from the group consisting of unsaturated carboxylic acids, esters of the unsaturated carboxylic acids, acid halides of the unsaturated carboxylic acids, and anhydrides of the unsaturated carboxylic acids, the reaction is preferably performed at 30 to 130° C. for 0.5 to 8 hours.

In the fluorine-containing monomer synthesis step, the amount of the fluorine-containing monomer of formula (5) produced as a minor reaction product may vary depending on the type of any of the unsaturated carboxylic acids and the like, the reaction temperature, and the reaction time.

If the amount of any of the unsaturated carboxylic acids and the like used is too small, the amount of the fluorine-containing monomer of formula (5) produced can be reduced, but a large amount of the unreacted diol of formula (3) may remain. Then, it is necessary to separate the fluorine-containing monomer of formula (4) from the diol of formula (3).

Also, if the amount of any of the unsaturated carboxylic acids used is too large, the amount of the fluorine-containing monomer of formula (5) produced can be increased. In addition, homopolymers of any of the unsaturated carboxylic acids and the like may be produced.

For these reasons, the molar ratio of the diol of formula (3) to the at least one selected from the group consisting of unsaturated carboxylic acids, esters of the unsaturated carboxylic acids, acid halides of the unsaturated carboxylic acids, and anhydrides of the unsaturated carboxylic acids used is preferably such that [the molar amount of the diol of formula (3) used]:[the molar amount of the at least one selected from the group consisting of unsaturated carboxylic acids, esters of the unsaturated carboxylic acids, acid halides of the unsaturated carboxylic acids, and anhydrides of the unsaturated carboxylic acids]=1:0.7 to 1:1.3.

Examples of compounds preferred as the fluorine-containing monomer of formula (4) obtained in the fluorine-containing monomer synthesis step include 5,5,5-trifluoro-4-hydroxy-4-trifluoromethylpentan-2-yl methacrylate, which is a fluorine-containing monomer represented by the following formula (4-1), and 1,1,1-trifluoro-2-hydroxy-2-trifluoromethylheptan-4-yl methacrylate, which is a fluorine-containing monomer represented by the following formula (4-2).

[Chem. 7]

(4-1)

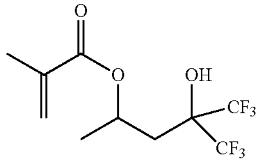

(4-2)

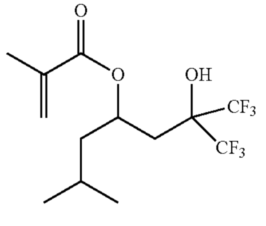

Fluorine-Containing Monomer Purification Step

Next, a fluorine-containing monomer purification step is performed in the method for producing a fluorine-containing polymer of the present disclosure.

The fluorine-containing monomer purification step includes removing the fluorine-containing monomer of formula (5) from the composition obtained in the fluorine-containing monomer synthesis step to adjust the amount of the fluorine-containing monomer of formula (5), expressed in parts per million based on the mass of the fluorine-containing monomer of formula (4), to 1500 ppm or less.

Moreover, the amount of the fluorine-containing monomer of formula (5) is preferably 450 ppm or less, more preferably 200 ppm or less. The amount of the fluorine-containing monomer of formula (5) is also more preferably 10 ppm or more.

The fluorine-containing monomer of formula (5) can cause lot-to-lot variation in the weight average molecular weight of the fluorine-containing polymer to be obtained through the subsequent steps.

When the amount of the fluorine-containing monomer of formula (5), expressed in parts per million based on the mass of the fluorine-containing monomer of formula (4), in the composition obtained after the fluorine-containing monomer synthesis step is adjusted to 1500 ppm or less, the lot-to-lot variation in the weight average molecular weight the fluorine-containing polymer to be obtained through the subsequent steps can be reduced.

The fluorine-containing monomer of formula (5) may be removed from the composition by any method such as column chromatography, precision distillation, crystallization, or other known methods. These methods may be combined in order to obtain the fluorine-containing monomer of formula (4) with high purity.

Each method is described in detail below.

Column Chromatography

A typical cylindrical base material for a column is filled with a filler, and the composition is passed therethrough with an organic solvent as a mobile phase to remove the fluorine-containing monomer of formula (5) from the composition.

The filler is preferably silica gel or alumina gel, more preferably alumina gel, but is not limited thereto. The filler may include one filler or two or more fillers.

The mobile phase may be a common organic solvent such as hexane, heptane, toluene, or ethyl acetate, but is not limited thereto. Moreover, the mobile phase may include one solvent or two or more solvents.

The column chromatography is preferably performed in the temperature range of 0° C. to 40° C., more preferably in the temperature range of 20° C. to 30° C.

Increasing the amount (height) of the added filler requires longer time, but improves the degree of separation. When the cylindrical base material for a column used is ILC-B22-300 (model number) available from Kiriyama Glass Works Co., the height of the filler is desirably 5 cm to 15 cm.

Precision Distillation

When the fluorine-containing monomer of formula (5) is removed from the composition by precision distillation, the number of theoretical stages of the distillation column is required to be at least 5 but not more than 40.

If the number of theoretical stages is less than 5, it is difficult to sufficiently remove the fluorine-containing monomer of formula (5). The larger the number of stages of the distillation column, the higher the ability to separate and remove the fluorine-containing monomer of formula (5). If the number of stages is more than 40, the ability to separate and remove approaches the upper limit, and the cost effectiveness is less likely to be improved.

Moreover, the fluorine-containing monomer of formula (4) may undergo a polymerization reaction during the precision distillation. Such a polymerization reaction may be prevented by adding a polymerization inhibitor to the composition.

Moreover, oxygen may be introduced into the distillation column.

Non-limiting examples of the polymerization inhibitor include o-cresol, m-cresol, p-cresol, 6-t-butyl-2,4-xylenol, 2,6-di-t-butyl-p-cresol, hydroquinone, catechol, 4-t-butylpyrocatechol, 2,5-bistetramethylbutylhydroquinone, 2,5-di-t-butylhydroquinone, p-methoxyphenol, 1,2,4-trihydroxybenzene, 1,2-benzoquinone, 1,3-benzoquinone, 1,4-benzoquinone, leucoquinizarin, phenothiazine, 2-methoxyphenothiazine, tetraethylthiuram disulfide, 1,1-diphenyl-2-picrylhydrazyl, and 1,1-diphenyl-2-picrylhydrazine.

Examples of commercially available polymerization inhibitors include products available from Seiko Chemical Co., Ltd. such as N,N'-di-2-naphthyl-p-phenylenediamine (trade name, Nonflex F), N,N-diphenyl-p-phenylenediamine (trade name, Nonflex H), 4,4'-bis(a,a-dimethylbenzyl)diphenylamine (trade name, Nonflex DCD), 2,2'-methylene-bis (4-methyl-6-tert-butylphenol) (trade name, Nonflex MBP), and N-(1-methylheptyl)-N'-phenyl-p-phenylenediamine (trade name, Ozonone 35), and products available from Wako Pure Chemical Industries, Ltd. such as ammonium N-nitrosophenylhydroxyamine (trade name, Q-1300) and an N-nitrosophenylhydroxyamine aluminum salt (trade name, Q-1301).

Any amount of the polymerization inhibitor may be used in the precision distillation. The amount of the polymerization inhibitor is preferably at least 0.01 parts by mass but not more than 5 parts by mass, more preferably at least 0.01 parts by mass but not more than 1 part by mass per 100 parts by mass of the fluorine-containing monomer of formula (4) when measured before the precision distillation.

If the amount of the polymerization inhibitor is less than 0.01 parts by mass per 100 parts by mass of the fluorine-containing monomer of formula (4), it is difficult to prevent the polymerization of the fluorine-containing monomer of formula (4).

If the amount of the polymerization inhibitor is more than 5 parts by mass per 100 parts by mass of the fluorine-containing monomer of formula (4), the effect of preventing the polymerization of the fluorine-containing monomer of formula (4) approaches the upper limit, and the cost effectiveness is less likely to be improved.

Here, the amount of the fluorine-containing monomer of formula (4) in the composition can be measured by gas chromatography.

Crystallization

The fluorine-containing monomer of formula (5) can be removed from the composition by crystallization.

The crystallization is an operation which can cause precipitation and crystal growth of the fluorine-containing monomer of formula (4) by dissolving the composition in a good solvent and adding a poor solvent or lowering the temperature.

The type of solvent used in the crystallization is not limited as long as the fluorine-containing monomer of formula (4) is readily soluble or insoluble in the solvent. Examples include alcohols, nitriles, ketones, amides, sulfoxides, ethers, hydrofluorocarbons, hydrofluoroethers, hydrocarbons, aromatic hydrocarbons, and water.

Examples of the alcohols include methanol, ethanol, n-propanol, isopropanol, ethylene glycol, and propylene glycol.

Examples of the nitriles include acetonitrile and benzonitrile.

Examples of the ketones include acetone, methyl ethyl ketone, diethyl ketone, methyl n-propyl ketone, methyl iso-propyl ketone, methyl n-butyl ketone, and methyl iso-butyl ketone.

Examples of the amides include N,N-dimethylformamide, N,N-dimethylacetamide, and N,N-dimethylimidazolidinone.

Examples of the sulfoxides include dimethyl sulfoxide.

Examples of the ethers include diethyl ether, methyl t-butyl ether, diisopropyl ether, dibutyl ether, and tetrahydrofuran.

Examples of the hydrofluorocarbons include trifluoromethane, difluoromethane, 1,1,1,2-tetrafluoroethane, 1,1,1-tetrafluoroethane, 1,1-difluoroethane, 1,1,1,2,3,3,3-heptafluoropropane, 1,1,1,3,3,3-hexafluoropropane, 1,1,1,3,3-heptafluoropropane, 1,1,1,3,3-pentafluorobutane, 1,1,1,2,2,3,4,5,5,5-decafluoropentane, and 1,1,2,2,3,3,4-heptafluorocyclopentane.

Examples of the hydrofluoroethers include methyl 1,1,2,2,2-pentafluoroethyl ether, methyl trifluoromethyl ether, methyl 1,1,2,2-tetrafluoroethyl ether, 1,1,2,2-tetrafluoro-1-(2,2,2-trifluoroethoxy)ethane, (2,2,3,3-tetrafluoropropyl) (1,1,2,3,3,3-hexafluoropropyl) ether, (methyl) (nonafluorobutyl) ether, (methyl) (nonafluoroisobutyl) ether, (ethyl) (nonafluorobutyl) ether, (ethyl) (nonafluoroisobutyl) ether, 1,1,1,2,2,3,4,5,5,5-decafluoro-3-methoxy-4-(trifluoromethyl)pentane, 2-trifluoromethyl-3-ethoxy-dodecafluorohexane, and 1,1,1,2,3-hexafluoro-4-(1,1,2,3,3,3-hexafluoropropoxy)pentane.

Examples of the hydrocarbons include butane, pentane, hexane, heptane, octane, nonane, and decane.

Examples of the aromatic hydrocarbons include benzene, toluene, xylene, mesitylene, and perfluorobenzene.

At least one compound selected from these solvents is preferably used as a good solvent or a poor solvent.

The amount of the solvent used in the crystallization is preferably at least 50 parts by mass but not more than 2000 parts by mass, more preferably at least 100 parts by mass but not more than 1000 parts by mass per 100 parts by mass of the fluorine-containing monomer of formula (4) when measured before the crystallization.

If the amount of the solvent is less than 50 parts by mass per 100 parts by mass of the fluorine-containing monomer of formula (4), it is difficult to stir and mix a slurry of the fluorine-containing monomer of formula (4) precipitated by crystallization.

Even if 100 parts by mass of the fluorine-containing monomer of formula (4) is dissolved by adding more than 2000 parts by mass of the solvent, the efficiency of removing impurities approaches the upper limit, and the cost effectiveness is less likely to be improved.

Here, the amount of the fluorine-containing monomer of formula (4) in the composition can be measured by gas chromatography.

It should be noted that the present disclosure also encompasses the composition obtained after the fluorine-containing monomer purification step, which contains the fluorine-containing monomer of formula (4), and the fluorine-containing monomer of formula (5) in an amount, expressed in parts per million based on the mass of the fluorine-containing monomer of formula (4), of 1500 ppm or less. Moreover, when a polymerization step is performed as described later, another monomer other than the fluorine-containing monomer of formula (4) and the fluorine-containing monomer of formula (5), and/or an organic solvent may be added to the composition. The present disclosure also encompasses the composition containing these.

Polymerization Step

Next, a polymerization step is performed in the method for producing a fluorine-containing polymer of the present disclosure.

The polymerization step includes polymerizing the fluorine-containing monomer of formula (4) from the composition obtained after the fluorine-containing monomer purification step to give a fluorine-containing polymer containing the repeating unit of formula (1).

Here, as the composition obtained after the fluorine-containing monomer purification step contains the fluorine-containing monomer of formula (5) that has not been completely removed therefrom, this fluorine-containing monomer of formula (5) will also be polymerized. Therefore, the resulting fluorine-containing polymer contains the repeating unit of formula (2).

As the fluorine-containing monomer of formula (4) from the composition containing a reduced amount of the fluorine-containing monomer of formula (5) is polymerized in the polymerization step, the lot-to-lot variation in the weight average molecular weight of the fluorine-containing polymer to be obtained can be reduced.

Here, any of the unsaturated carboxylic acids and the like added to the fluorine-containing alcohol moiety containing a fluorine atom in the fluorine-containing monomer of formula (5) may be polymerized in the polymerization step.

Thus, the resulting fluorine-containing polymer may contain a repeating unit represented by the following formula (8):

[Chem. 8]

(8)

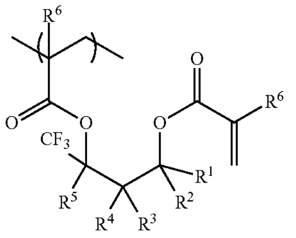

wherein $R^1$ and $R^2$ are each independently a hydrogen atom, a methyl group, an ethyl group, an n-propyl group, an iso-propyl group, an n-butyl group, an iso-butyl group, a sec-butyl group, or a t-butyl group; $R^3$ and $R^4$ are each independently a hydrogen atom, a methyl group, or an ethyl group; $R^5$ is a hydrogen atom or a trifluoromethyl group; and $R^6$ is a hydrogen atom, a chlorine atom, a methyl group, or a trifluoromethyl group.

Moreover, any of the unsaturated carboxylic acids and the like added to the alkyl alcohol moiety containing no fluorine atom and any of the unsaturated carboxylic acids and the like added to the fluorine-containing alcohol moiety containing a fluorine atom in the fluorine-containing monomer of formula (5) may be both polymerized in the polymerization step.

Thus, the resulting fluorine-containing polymer may contain such a repeating unit.

In the polymerization step, another monomer other than the fluorine-containing monomer of formula (4) and the fluorine-containing monomer of formula (5) may be added to the composition obtained after the fluorine-containing monomer purification step, and a polymerization reaction of this composition may be performed.

Examples of the another monomer other than the fluorine-containing monomer of formula (4) and the fluorine-containing monomer of formula (5) include the following monomers:

monomers having a hexafluoroisopropanol group ($-C(CF_3)_2OH$), acrylic acid esters, methacrylic acid esters, fluorine-containing acrylic acid esters, fluorine-containing methacrylic acid esters, styrenes, fluorine-containing styrenes, vinyl ethers, fluorine-containing vinyl ethers, allyl ethers, fluorine-containing allyl ethers, unsaturated amides, olefins, fluorine-containing olefins, norbornene compounds, fluorine-containing norbornene compounds, vinylsilanes, vinylsulfonic acid or vinylsulfonic acid esters, acrylic acid, methacrylic acid, maleic acid, maleic anhydride, fumaric acid, and sulfur dioxide.

The another monomer used may also be a monomer containing an acid-decomposable group.

When a fluorine-containing polymer is produced with a monomer containing an acid-decomposable group and used as a resist, the resist film formed on a substrate can be exposed to high-energy rays such as an electron beam or an electromagnetic wave with a wavelength of 300 nm or less to generate an acid in the resist film due to decomposition of the acid-decomposable group.

This acid may improve the solubility of the exposed area of the resist film in an alkaline developer in development.

The another monomer used may also be a monomer having a lactone structure.

When a fluorine-containing copolymer is produced with a monomer having a lactone structure and used as a resist, the adhesion between the resist film containing the fluorine-containing copolymer and a substrate can be improved. Further, when the fluorine-containing copolymer is used as a composition for forming an overlying film to form an overlying film on a resist pattern, not only can the adhesion to the underlying resist pattern be improved, but also the affinity with a developer in development can be increased and a high-resolution resist pattern can be obtained.

One such another monomer or two or more such another monomers may be added.

Examples of the monomers having a hexafluoroisopropanol group include the following monomers:

[Chem. 9]

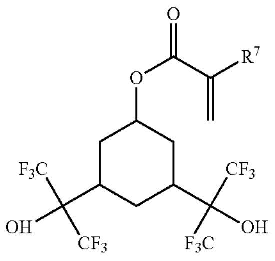

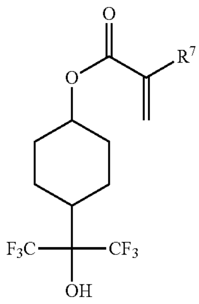

-continued

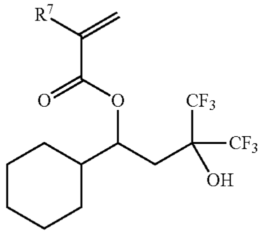

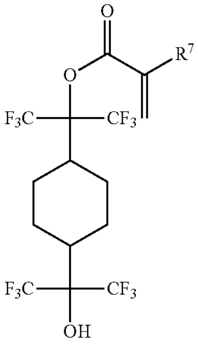

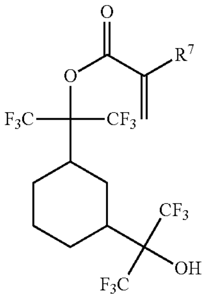

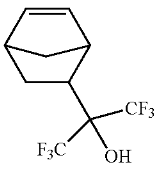

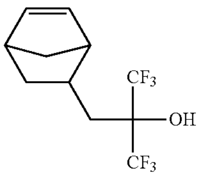

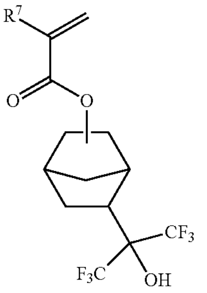

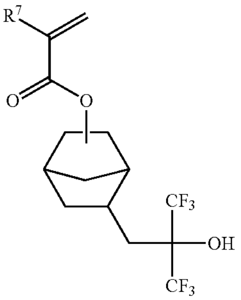

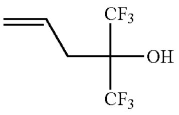

wherein $R^7$ is a hydrogen atom, a methyl group, a fluorine atom, or a trifluoromethyl group, and the hydrogen atom of the hydroxy group may be replaced by a protecting group.

Examples of the acrylic acid esters include methyl acrylate, ethyl acrylate, n-propyl acrylate, isopropyl acrylate, n-butyl acrylate, isobutyl acrylate, n-hexyl acrylate, n-octyl acrylate, 2-ethylhexyl acrylate, lauryl acrylate, 2-hydroxyethyl acrylate, 2-hydroxypropyl acrylate, tert-butyl acrylate, 3-oxocyclohexyl acrylate, adamantyl acrylate, methyladamantyl acrylate, ethyladamantyl acrylate, hydroxyadamantyl acrylate, cyclohexyl acrylate, and tricyclodecanyl acrylate.

Examples of the methacrylic acid esters include methyl methacrylate, ethyl methacrylate, n-propyl methacrylate, isopropyl methacrylate, n-butyl methacrylate, isobutyl methacrylate, n-hexyl methacrylate, n-octyl methacrylate, 2-ethylhexyl methacrylate, lauryl methacrylate, 2-hydroxyethyl methacrylate, 2-hydroxypropyl methacrylate, tert-butyl methacrylate, 3-oxocyclohexyl methacrylate, adamantyl methacrylate, methyladamantyl methacrylate, ethyladamantyl methacrylate, hydroxyadamantyl methacrylate, cyclohexyl methacrylate, and tricyclodecanyl methacrylate.

Examples of the fluorine-containing acrylic acid esters and fluorine-containing methacrylic acid esters include acrylic or methacrylic acid esters containing a fluorine atom or a fluorine-containing alkyl group at the α-position of the acrylic structure, and acrylic or methacrylic acid esters containing a fluorine atom or a fluorine-containing alkyl group in the ester structure.

The fluorine-containing acrylic or methacrylic acid esters may contain a fluorine atom or a fluorine-containing alkyl group both at the α-position of the acrylic structure and in the ester moiety. Also, a cyano group may be introduced at the α-position of the acrylic structure.

Specific examples of the fluorine-containing alkyl group to be introduced at the α-position of the acrylic structure in the fluorine-containing acrylic or methacrylic acid esters include a trifluoromethyl group, a trifluoroethyl group, and a nonafluoro-n-butyl group.

The ester structure in the fluorine-containing acrylic or methacrylic acid esters may have a fluorinated alkyl group such as a perfluoroalkyl group or a fluoroalkyl group. Moreover, the ester structure may contain both a cyclic structure and a fluorine atom. Further, the cyclic structure may have a ring such as a fluorine-containing benzene ring, a fluorine-containing cyclopentane ring, a fluorine-containing cyclohexane ring, or a fluorine-containing cycloheptane ring, each having a fluorine atom, a trifluoromethyl group, a hexafluoroisopropyl hydroxy group, etc. The ester structure may also be a t-butyl ester group having a fluorine atom.

Examples of such fluorine-containing acrylic acid esters include 2,2,2-trifluoroethyl acrylate, 2,2,3,3-tetrafluoropropyl acrylate, 1,1,1,3,3,3-hexafluoroisopropyl acrylate, heptafluoroisopropyl acrylate, 1,1-dihydroheptafluoro-n-butyl acrylate, 1,1,5-trihydrooctafluoro-n-pentyl acrylate, 1,1,2,2-tetrahydrotridecafluoro-n-octyl acrylate, 1,1,2,2-tetrahydroheptadecafluoro-n-decyl acrylate, perfluorocyclohexylmethyl acrylate, 6-[3,3,3-trifluoro-2-hydroxy-2-(trifluoromethyl)propyl]bicyclo[2.2.1]heptyl-2-yl acrylate, 6-[3,3,3-trifluoro-2-hydroxy-2-(trifluoromethyl)propyl]bicyclo[2.2.1]heptyl-2-yl-2-(trifluoromethyl)acrylate, and 3,5-bis(1,1,1,3,3,3-hexafluoro-2-hydroxyisopropyl)cyclohexyl-2-trifluoromethyl acrylate.

Examples of the fluorine-containing methacrylic acid esters include 2,2,2-trifluoroethyl methacrylate, 2,2,3,3-tetrafluoropropyl methacrylate, 1,1,1,3,3,3-hexafluoroisopropyl methacrylate, heptafluoroisopropyl methacrylate, 1,1-dihydroheptafluoro-n-butyl methacrylate, 1,1,5-trihydrooctafluoro-n-pentyl methacrylate, 1,1,2,2-tetrahydrotridecafluoro-n-octyl methacrylate, 1,1,2,2-tetrahydroheptadecafluoro-n-decyl methacrylate, perfluorocyclohexylmethyl methacrylate, 6-[3,3,3-trifluoro-2-hydroxy-2-(trifluoromethyl)propyl]bicyclo[2.2.1]heptyl-2-yl methacrylate, 3,5-bis(1,1,1,3,3,3-hexafluoro-2-hydroxyisopropyl)cyclohexyl acrylate, and 3,5-bis(1,1,1,3,3,3-hexafluoro-2-hydroxyisopropyl)cyclohexyl methacrylate.

Examples of the styrenes and fluorine-containing styrenes include styrene, hydroxystyrene, and fluorinated styrenes.

Examples of the fluorinated styrenes include styrenes in which hydrogen atoms of the aromatic ring are replaced by a fluorine atom or a trifluoromethyl group such as pentafluorostyrene, trifluoromethylstyrene, and bistrifluoromethylstyrene. Other examples include styrenes in which hydrogen atoms of the aromatic ring are replaced by a hexafluoroisopropanol group or a hexafluoroisopropanol group whose hydroxy group is protected with a protecting group. Also usable are the above-described styrenes in which a halogen, an alkyl group, or a fluorine-containing alkyl group is bonded at the α-position, and styrenes containing a perfluorovinyl group.

The vinyl ethers, fluorine-containing vinyl ethers, allyl ethers, and fluorine-containing allyl ethers may have a methyl group, an ethyl group, a propyl group, a butyl group, or a hydroxy group such as a hydroxyethyl group or a hydroxybutyl group in the structure.

These compounds may also contain in the structure a cyclic vinyl or allyl ether having a cyclohexyl group, a norbornyl group, an aromatic ring, or the ring structure thereof containing hydrogen or a carbonyl bond. The hydrogen atoms of the foregoing groups may be partially or fully replaced by a fluorine atom.

Examples of the unsaturated amides include acrylamide, methacrylamide, N-methylolacrylamide, N-methylolmethacrylamide, and diacetone acrylamide.

Examples of the olefins include ethylene, propylene, isobutene, cyclopentene, and cyclohexene.

Examples of the fluorine-containing olefins include vinyl fluoride, vinylidene fluoride, trifluoroethylene, chlorotrifluoroethylene, tetrafluoroethylene, hexafluoropropylene, and hexafluoroisobutene.

The monomers having a norbornene moiety may contain one or more norbornene moieties in which a hydrogen atom may be replaced by a fluorine-containing functional group.

Examples of such monomers include norbornene compounds synthesized by Diels-Alder addition reactions of cyclopentadiene or cyclohexadiene and unsaturated compounds.

Examples of the unsaturated compounds used in the synthesis of the norbornene compounds include acrylic acid, methacrylic acid, α-fluoroacrylic acid, α-trifluoromethylacrylic acid, acrylic acid esters, methacrylic acid esters, fluorine-containing acrylic acid esters, fluorine-containing methacrylic acid esters, fluorine-containing olefins, allyl alcohols, fluorine-containing allyl alcohols, homoallyl alcohols, fluorine-containing homoallyl alcohols, 2-(benzoyloxy)pentafluoropropane, 2-(methoxyethoxymethyloxy)pentafluoropropene, 2-(tetrahydroxypyranyloxy)pentafluoropropene, 2-(benzoyloxy) trifluoroethylene, 2-(methoxymethyloxy)trifluoroethylene, and 3-(5-bicyclo[2.2.1]hepten-2-yl)-1,1,1-trifluoro-2-(trifluoromethyl)-2-propanol.

The acid-decomposable group in the monomer containing an acid-decomposable group may be any group that can be hydrolyzed by an acid generated from the photoacid generator in the resist and detached from the fluorine-containing polymer. As such an acid-decomposable group, the monomer preferably has an acid-decomposable group represented by the following formula (9) or (10):

[Chem. 10]

(9)

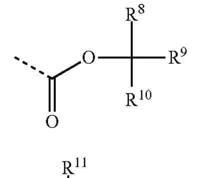

(10)

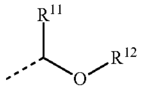

wherein $R^8$, $R^9$, $R^{10}$, and $R^{12}$ are each independently a C1-C25 linear alkyl group or a C3-C25 branched or cyclic alkyl group, in which the hydrogen atoms in the alkyl group may be partially or fully replaced by a fluorine atom, an oxygen atom, a nitrogen atom, a sulfur atom, or a hydroxy group; any two of $R^8$, $R^9$, and $R^{10}$ may be bonded to each other to form a ring; $R^{11}$ is a hydrogen atom, a C1-C25 linear alkyl group, or a C3-C25 branched or cyclic alkyl group, in which the hydrogen atoms in the alkyl group may be partially or fully replaced by a fluorine atom, an oxygen atom, a nitrogen atom, a sulfur atom, or a hydroxy group; and the dotted lines represent bonds.

Specific examples of the acid-decomposable groups of formulas (9) and (10) include the acid-decomposable groups listed below. Here, the dotted lines represent bonds.

[Chem. 11]

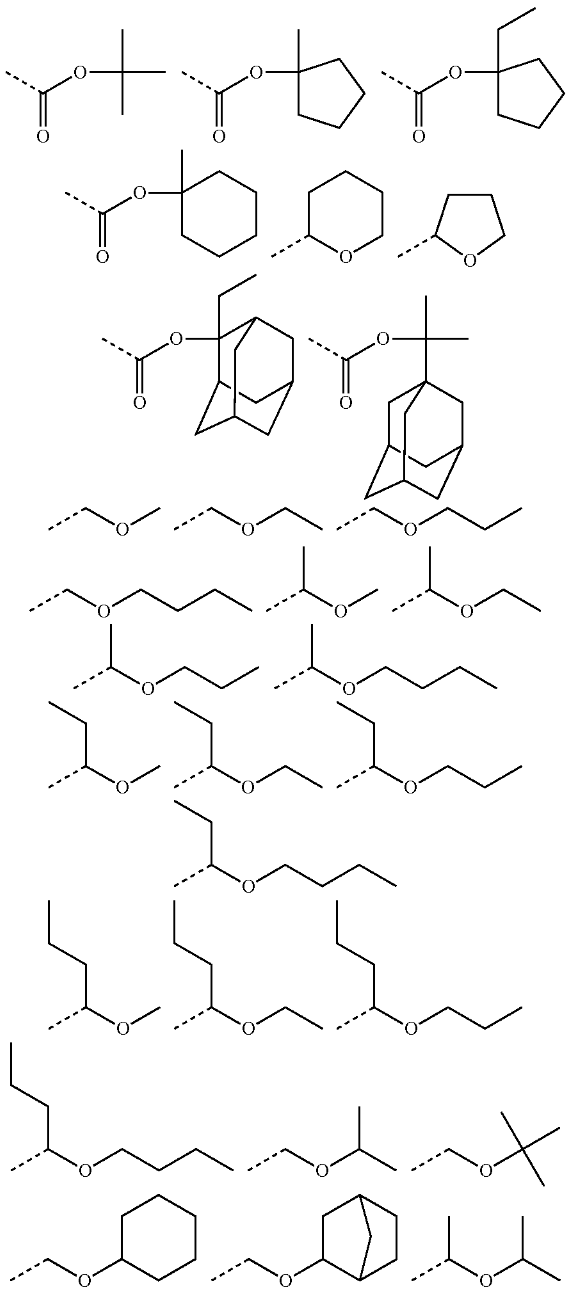

-continued

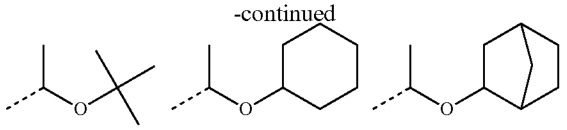

Examples of the monomer having a lactone structure include monomers having a monocyclic lactone structure such as a group obtained by removing one hydrogen atom from γ-butyrolactone or mevalonic lactone, and monomers having a polycyclic lactone structure such as a group obtained by removing one hydrogen atom from norbornane lactone.

Among the another monomers described above, 3,5-bis(1,1,1,3,3,3-hexafluoro-2-hydroxyisopropyl)cyclohexyl methacrylate represented by the following formula (11) and 1,1,2,2-tetrahydroheptadecafluoro-n-decyl acrylate represented by the following formula (12) are preferred.

[Chem. 12]

(11)

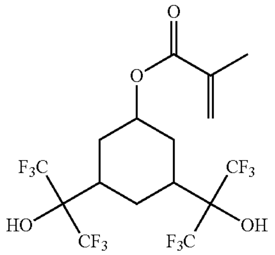

(12)

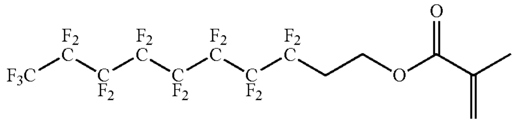

When 3,5-bis(1,1,1,3,3,3-hexafluoro-2-hydroxyisopropyl)cyclohexyl methacrylate is added and the resulting fluorine-containing polymer is used as a component of a resist film or an overlying film, the following effects can be obtained: an increase in solubility in the organic solvent used in the preparation of a coating liquid, and improvement of solubility in the developer used in development.

When 1,1,2,2-tetrahydroheptadecafluoro-n-decyl acrylate is added and the resulting fluorine-containing polymer is used as a component of an overlying film, the adhesion of the overlying film to the underlying resist film can be improved, and the water repellency of the surface of the overlying film can be improved, so that the exposure time can be shortened in immersion exposure using water as the exposure medium. In addition, the surface tension can be reduced, the surface of the overlying film can be smoothed, and the film thickness can be made uniform.

When another monomer is added, the amount thereof is not limited, but the percentage of the repeating unit derived from the another monomer based on 100 mol % of the total repeating units in the fluorine-containing polymer after the polymerization is preferably at least 1 mol % but not more than 80 mol %, more preferably at least 5 mol % but not more than 70 mol %, even more preferably at least 10 mol % but not more than 60 mol %.

If the percentage of the repeating unit derived from the another monomer is less than 1 mol %, the following effects expected when the fluorine-containing polymer is used as a resist can be inhibited: improvement of solubility in an organic solvent, improvement of the adhesion between a substrate and the resist film formed on the substrate, and improvement of the etching resistance of the resist pattern.

If the percentage of the repeating unit derived from the another monomer is more than 80 mol %, the percentage of the repeating unit of formula (1) is reduced so that the effect of improving the transparency of the resist film and the effect of improving the solvent solubility can be inhibited.

Non-limiting examples of the polymerization reaction in the polymerization step include a radical polymerization reaction, an ionic polymerization reaction, a coordinated anionic polymerization reaction, a living anionic polymerization reaction, and a cationic polymerization reaction.

A radical polymerization reaction is preferred among these.

When the polymerization reaction is a radical polymerization reaction, any polymerization initiator may be used as long as it can allow the polymerization reaction to occur. The polymerization initiator may be an azo compound, a peroxide compound, or a redox compound.

Examples of the azo compound include azobisisobutyronitrile.

Examples of the peroxide compound include t-butyl peroxypivalate, di-t-butyl peroxide, i-butyryl peroxide, lauroyl peroxide, succinic acid peroxide, dicinnamyl peroxide, di-n-propyl peroxydicarbonate, t-butyl peroxyallyl monocarbonate, benzoyl peroxide, hydrogen peroxide, and ammonium persulfate.

As the redox compound, a combination of an oxidizing agent and a reducing agent may be used. Examples of the oxidizing agent compound include hydrogen peroxide, persulfates, and cumene hydroperoxide. Examples of the reducing agent compound include iron (II) ionic salts, copper (I) ionic salts, ammonia, and triethylamine.

In the radical polymerization reaction, a polymerization solvent may also be used.

The polymerization solvent may be any one as long as it does not inhibit the radical polymerization reaction, and may be an organic solvent or water.

Examples of the organic solvent include hydrocarbon solvents, ester solvents, ketone solvents, alcohol solvents, ether solvents, cyclic ether solvents, fluorocarbon solvents, and aromatic solvents.

These solvents may be used alone or in combinations of two or more.

Examples of the ester solvents include acetic acid and n-butyl acetate.

Examples of the ketone solvents include acetone and methyl isobutyl ketone.

Examples of the hydrocarbon solvents include toluene and cyclohexane.

Examples of the alcohol solvents include methanol, isopropyl alcohol, and ethylene glycol monomethyl ether.

In the radical polymerization reaction, a molecular weight modifier such as mercaptan may also be used.

Although the reaction temperature in the radical polymerization reaction may be appropriately changed depending on the type of radical polymerization initiator or radical polymerization initiator, it is preferably at least 20° C. but not higher than 200° C., more preferably at least 30° C. but not higher than 140° C.

After the polymerization step, the organic solvent or water as the medium may be removed from the solution or dispersion containing the synthesized fluorine-containing polymer by a known method.

Specific examples of the method include reprecipitation, filtration, and thermal distillation under reduced pressure.

Through the above steps, a fluorine-containing polymer containing the repeating unit of formula (1) and the repeating unit of formula (2) can be produced.

In the polymerization step in the method for producing a fluorine-containing polymer of the present disclosure, the fluorine-containing polymer is preferably synthesized such that the relative standard deviation, which is the numerical value obtained by dividing the standard deviation of the weight average molecular weight of the fluorine-containing polymer to be obtained by the average weight average molecular weight of the fluorine-containing polymer, is 0.10 to 1.10. More preferably, the relative standard deviation is 0.10 to 0.60.

Herein, the term "standard deviation of the weight average molecular weight of the fluorine-containing polymer to be obtained" refers to the standard deviation of the weight average molecular weight of the fluorine-containing polymer produced in six lots under the same conditions.

Moreover, the weight average molecular weight of the fluorine-containing polymer herein refers to the numerical value measured by gel permeation chromatography (GPC) under the following conditions.

GPC Conditions

Apparatus: HLC-8320GPC available from Tosoh Corporation

Column for polymerizable monomer analysis: TSKgel series (G2500HXL, G2000HXL, G1000HXL, and G1000HXL connected in series in this order) available from Tosoh Corporation Column for polymer analysis: TSKgel series (G2500HXL, G2000HXL, G1000HXL, and G1000HXL connected in series in this order) available from Tosoh Corporation Temperature program: 40° C. (hold)

Flow rate: 1 mL/min

Detector: Differential refractometer (RI)

Eluent: Tetrahydrofuran (THF)

Reference substance: Polystyrene standard solutions

The relative standard deviation of 0.10 to 1.10 can be achieved by sufficiently removing the fluorine-containing monomer of formula (5) from the composition in the fluorine-containing monomer purification step in the method for producing a fluorine-containing polymer of the present disclosure.

The thus obtained fluorine-containing polymer has little lot-to-lot variation in weight average molecular weight. Thus, when the fluorine-containing polymer is used to form a resist pattern, the alkali solubility is less likely to vary and the exposure and development conditions can be easily adjusted. Further, when a fine resist pattern is formed, unevenness is less likely to occur in the pattern obtained after the development step.

Moreover, when a fluorine-containing polymer whose weight average molecular weight varies from lot to lot is used to form a fine resist pattern, unevenness may occur in the pattern obtained after the development step.

However, the fluorine-containing polymer produced by the method for producing a fluorine-containing polymer of the present disclosure has little lot-to-lot variation in weight average molecular weight. Thus, when a fine resist pattern is formed from the fluorine-containing polymer obtained in the present disclosure, the pattern surface obtained after the development step provides good smoothness.

The weight average molecular weight of the obtained fluorine-containing polymer is preferably 5000 to 20000, more preferably 7000 to 12000.

The obtained fluorine-containing polymer can be used as a component of a resist film or an overlying film for protecting a resist pattern.

Moreover, the resist film or resist pattern formed from the obtained fluorine-containing polymer has high transparency and high solvent solubility.

Particular non-limiting examples of the present disclosure will be described below.

Preparation of Standard Sample of Monomer of Formula (4)

Fluorine-Containing Monomer Synthesis Step

A 1 L three-necked flask equipped with a thermometer, a reflux condenser, and a stirrer was charged with 100 g (0.44 mol) of 1,1,1-trifluoro-2-(trifluoromethyl)pentane-1,3-diol (a compound represented by the following formula (3-1)), 74.6 g (0.48 mol) of methacrylic anhydride, 4.2 g (0.044 mol) of methanesulfonic acid, 400 g of toluene, and 0.5 g of phenothiazine. Thereafter, the bottom of the three-necked flask was immersed in an oil bath adjusted at a temperature of 50° C., and the contents were reacted for four hours with stirring to obtain a composition.

The composition was measured by gas chromatography and the reaction solution was found to contain 94.5% by mass of 5,5,5-trifluoro-4-hydroxy-4-trifluoromethylpentan-2-yl methacrylate (a compound represented by the following formula (4-1)), 1.6% by mass of 1,1,1-trifluoro-2-(trifluoromethyl)pentane-1,3-diol, 2.0% by mass of methacrylic anhydride, and 1.9% by mass of other compounds, except for methacrylic acid as a minor reaction product.

[Chem. 13]

(4-1)

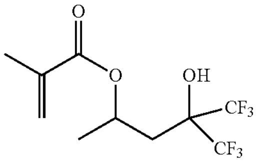

94.5%

(3-1)

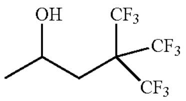

1.6%

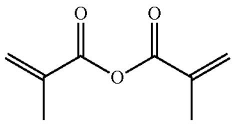

Methacrylic anhydride
2.0%

Fluorine-Containing Monomer Purification Step

The resulting composition was placed in a separatory funnel and washed twice with 400 g of sodium bicarbonate water. Then, the organic layer was collected and dried with 30 g of magnesium sulfate. The magnesium sulfate was removed by filtration. To the filtrate was added 0.7 g of phenothiazine as a polymerization inhibitor, the solvent was evaporated off, and then distillation under reduced pressure (8 Torr=1.1 kPa) was performed to collect a fraction at 80° C. to 82° C. Thus, 112 g of the fraction was obtained. The yield was 87%.

The fraction was analyzed with a gas chromatography-mass spectrometer (GC-MS) and found to be as shown below: the purity of the target product 5,5,5-trifluoro-4-hydroxy-4-trifluoromethylpentan-2-yl methacrylate (the fluorine-containing monomer of formula (4-1)) was 97.0% and 1,1,1-trifluoro-2-(trifluoromethyl)pentane-2,4-diyl methacrylate (a fluorine-containing monomer represented by the following formula (5-1)) as a minor reaction product was present.

[Chem. 14]

(5-1)

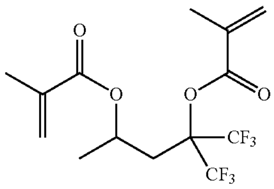

The above operation was repeated to produce 3.0 kg of a fraction containing 5,5,5-trifluoro-4-hydroxy-4-trifluoromethylpentan-2-yl methacrylate (the fluorine-containing monomer of formula (4-1)).

The resulting fraction was subjected to precision distillation in an Oldershaw distillation column to obtain 2.76 kg of a fraction having a boiling point of 80° C. at a pressure of 0.5 kPa.

The resulting fraction was measured by GC-MS and found to contain 5,5,5-trifluoro-4-hydroxy-4-trifluoromethylpentan-2-yl methacrylate (the fluorine-containing monomer of formula (4-1)) with a purity of 99.8%.

The concentration of 1,1,1-trifluoro-2-(trifluoromethyl) pentane-2,4-diyl methacrylate (the fluorine-containing monomer of formula (5-1)) measured by GC-MS before the precision distillation was 2600 ppm, while the concentration thereof after the precision distillation was decreased to 10 ppm. Thus, a composition containing 5,5,5-trifluoro-4-hydroxy-4-trifluoromethylpentan-2-yl methacrylate (the fluorine-containing monomer of formula (4-1)) whose purity had been increased by precision distillation was obtained. The composition was used as a standard sample of 5,5,5-trifluoro-4-hydroxy-4-trifluoromethylpentan-2-yl methacrylate (the fluorine-containing monomer of formula (4-1)).

Moreover, a standard sample of 1,1,1-trifluoro-2-(trifluoromethyl)pentane-2,4-diyl methacrylate (the fluorine-containing monomer of formula (5-1)) was prepared by the following method.

A 1 L three-necked flask equipped with a thermometer, a reflux condenser, and a stirrer was charged with 100 g of the standard sample of 5,5,5-trifluoro-4-hydroxy-4-trifluoromethylpentan-2-yl methacrylate (the fluorine-containing monomer of formula (4-1)) and then with 60 g of triethylamine, 4 g of N,N-dimethylaminopyridine, and 1 g of phenothiazine. The bottom of the flask was immersed in an ice bath, and 79 g of methacrylic anhydride was added dropwise with stirring. Then, the contents were returned to room temperature and stirred for one hour to obtain a reaction solution. The reaction solution was transferred to a separatory funnel and diluted with 300 g of toluene. Then, 200 mL of dilute hydrochloric acid was added thereto to terminate the reaction. The organic layer was separated. The separated organic layer was washed twice with 200 g of water, and then the solvent was evaporated off with a rotary evaporator. Then, distillation was performed in a distillation apparatus equipped with a Vigreux column. A fraction at 86° C. to 88° C. was collected at a reduced pressure of 0.5 kPa to obtain 16 g of oil. The oil was measured by GC-MS and found to contain 96% by mass of 1,1,1-trifluoro-2-(trifluoromethyl)pentane-2,4-diyl methacrylate (the fluorine-containing monomer of formula (5-1)) and 2.5% by mass of unreacted 5,5,5-trifluoro-4-hydroxy-4-trifluoromethylpentan-2-yl methacrylate (the fluorine-containing monomer of formula (4-1)). The oil was used as a standard sample of 1,1,1-trifluoro-2-(trifluoromethyl)pentane-2,4-diyl methacrylate (the fluorine-containing monomer of formula (5-1)).

Preparation of Raw Material Composition to be Used in Polymerization Step

The prepared standard sample of 5,5,5-trifluoro-4-hydroxy-4-trifluoromethylpentan-2-yl methacrylate (the fluorine-containing monomer of formula (4-1)) and the prepared standard sample of 1,1,1-trifluoro-2-(trifluoromethyl)pentane-2,4-diyl methacrylate (the fluorine-containing monomer of formula (5-1)) were used to prepare raw material compositions A to F at the ratios shown in Table 1.

TABLE 1

| Raw material composition | Purity of fluorine-containing monomer of formula (4-1) Purity (%) | Concentration of fluorine-containing monomer of formula (5-1) (ppm) |
|---|---|---|
| A | 99.8 | 10 |
| B | 99.8 | 100 |
| C | 99.8 | 400 |
| D | 99.8 | 500 |
| E | 99.7 | 1000 |
| F | 99.6 | 2000 |

EXAMPLE 1

Polymerization Step

At room temperature (about 20° C.), a 500 mL vessel was charged with 100 g of the raw material composition A. To the vessel was added 200 g of 2-butanone containing 6.26 g of dimethyl-2,2'-azobis(2-methylpropionate) (Wako Pure Chemical Industries, Ltd., product name V-601) dissolved therein to give a raw material composition A solution. The solution was transferred to a dropping funnel. Next, the dropping funnel was attached to a 500 mL reactor that was separately charged with 100 g of 2-butanone, and the 2-butanone was heated to 78° C.

While the temperature of the 2-butanone in the reactor was maintained at 78±1° C., the raw material composition A solution was gradually added dropwise to the reactor from the dropping funnel over two hours under a nitrogen stream. After completion of the dropwise addition, the mixture was maintained at a temperature of 78±1° C. for six hours and then cooled. Here, the mixture was gradually cooled to 30° C. over 30 minutes. Thus, a fluorine-containing polymer containing a repeating unit represented by the following formula (1-1) was obtained. The fluorine-containing polymer was used as a fluorine-containing polymer according to Example 1.

The weight average molecular weight of the fluorine-containing polymer according to Example 1 was measured by gel permeation chromatography (GPC) and found to be 9575 (N=1).

[Chem. 15]

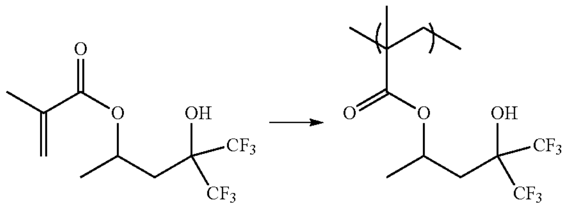

(4-1) (1-1)

In the same manner, the production of a fluorine-containing polymer according to Example 1 was performed five times (N=2 to 6), for a total of six times. The weight average molecular weight of the fluorine-containing polymer according to Example 1 obtained in each production was measured. Moreover, the relative standard deviation (RSD) was calculated, which is the numerical value obtained by dividing the standard deviation of the weight average molecular weight of the fluorine-containing polymer by the average weight average molecular weight of the fluorine-containing polymer. Table 2 shows the results.

Next, the reaction solution containing the fluorine-containing polymer was gradually added dropwise to n-heptane adjusted at a temperature of 25° C. over one hour with stirring, followed by stirring for an additional one hour. Thus, a fluorine-containing polymer slurry was obtained. The slurry was filtered under reduced pressure to obtain a cake. The cake was dried to obtain powder of the fluorine-containing polymer according to Example 1.

EXAMPLE 2 TO EXAMPLE 5

Fluorine-containing polymers according to Examples 2 to 5 were produced as in Example 1, except that the raw material compositions B to E, respectively, were used instead of the raw material composition A. Then, the weight average molecular weights of the fluorine-containing polymers according to Examples 2 to 5 were measured, and the relative standard deviations thereof were calculated, each of which is the numerical value obtained by dividing the standard deviation of the weight average molecular weight of the fluorine-containing polymer by the average weight average molecular weight of the fluorine-containing polymer. Table 2 shows the results.

EXAMPLE 6

At room temperature (about 20° C.), a 500 mL vessel was charged with 80 g of the raw material composition A and 20 g of 3,5-bis(1,1,1,3,3,3-hexafluoro-2-hydroxyisopropyl)cyclohexyl methacrylate (a monomer of formula (11)). To the vessel was added 200 g of 2-butanone containing 6.26 g of dimethyl-2,2'-azobis(2-methylpropionate) (Wako Pure Chemical Industries, Ltd., product name V-601) dissolved therein to give a solution mixture with the raw material composition A. The solution mixture was transferred to a dropping funnel. Next, the dropping funnel was attached to a 500 mL reactor that was separately charged with 100 g of 2-butanone, and the 2-butanone was heated to 78° C.

While the temperature of the 2-butanone in the reactor was maintained at 78±1° C., the solution mixture was gradually added dropwise to the reactor from the dropping funnel over two hours under a nitrogen stream. After completion of the dropwise addition, the mixture was maintained at a temperature of 78±1° C. for six hours and then cooled. Here, the mixture was gradually cooled to 30° C. over 30 minutes. Thus, a fluorine-containing polymer containing a repeating unit represented by the following formula (1-1) and a repeating unit represented by the following formula (11-1) was obtained. The fluorine-containing polymer was used as a fluorine-containing polymer according to Example 6.

Next, the 2-butanone was removed from the reaction solution, and the molecular weight of the fluorine-containing polymer according to Example 6 was measured by GPC and found to be 9669 (N=1).

[Chem. 16]

(1-1)

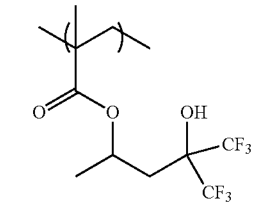

(11-1)

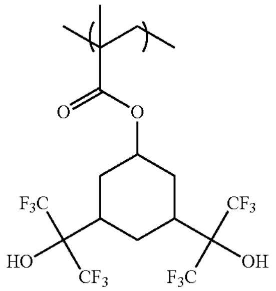

In the same manner, the production of a reaction solution of a fluorine-containing polymer according to Example 6 was performed five times (N=2 to 6), for a total of six times. The weight average molecular weight of the fluorine-containing polymer according to Example 6 obtained in each production was measured. Moreover, the relative standard deviation was calculated, which is the numerical value obtained by dividing the standard deviation of the weight average molecular weight of the fluorine-containing polymer by the average weight average molecular weight of the fluorine-containing polymer. Table 2 shows the results.

EXAMPLE 7

A fluorine-containing polymer according to Example 7 was produced as in Example 6, except that the raw material composition C was used instead of the raw material composition A. Then, the weight average molecular weight of the fluorine-containing polymer according to Example 7 was measured, and the relative standard deviation was calculated, which is the numerical value obtained by dividing the standard deviation of the weight average molecular weight of the fluorine-containing polymer by the average weight average molecular weight of the fluorine-containing polymer. Table 2 shows the results.

EXAMPLE 8

At room temperature (about 20° C.), a 500 mL vessel was charged with 95 g of the raw material composition A and 5 g of 1,1,2,2-tetrahydroheptadecafluoro-n-decyl acrylate (a monomer of formula (12)). To the vessel was added 200 g of 2-butanone containing 6.26 g of dimethyl-2,2'-azobis(2-methylpropionate) dissolved therein to give a solution mixture with the raw material composition A. The solution mixture was transferred to a dropping funnel. Next, the dropping funnel was attached to a 500 mL reactor that was separately charged with 100 g of 2-butanone, and the 2-butanone was heated to 78° C.

While the temperature of the 2-butanone in the reactor was maintained at 78±1° C., the solution mixture was gradually added dropwise to the reactor from the dropping funnel over two hours under a nitrogen stream. After completion of the dropwise addition, the mixture was maintained at a temperature of 78±1° C. for six hours and then cooled. Here, the mixture was gradually cooled to 30° C. over 30 minutes. Thus, a fluorine-containing polymer containing a repeating unit represented by the following formula (1-1) and a repeating unit represented by the following formula (12-1) was obtained. The fluorine-containing polymer was used as a fluorine-containing polymer according to Example 8.

The weight average molecular weight of the fluorine-containing copolymer according to Example 8 obtained by removing the 2-butanone from the reaction solution was measured by gel permeation chromatography (GPC) and found to be 9532 (N=1).

[Chem. 17]

(1-1)

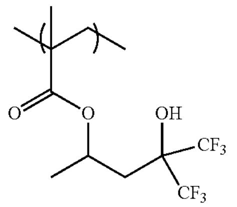

(12-1)

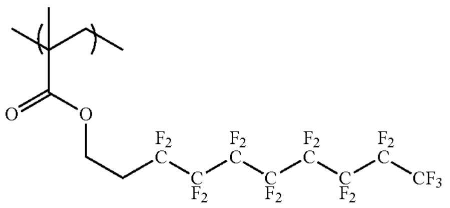

In the same manner, the production of a reaction solution of a fluorine-containing polymer according to Example 8 was performed five times (N=2 to 6), for a total of six times. The weight average molecular weight of the fluorine-containing polymer according to Example 8 obtained in each production was measured. Moreover, the relative standard deviation was calculated, which is the numerical value obtained by dividing the standard deviation of the weight average molecular weight of the fluorine-containing polymer by the average weight average molecular weight of the fluorine-containing polymer. Table 2 shows the results.

EXAMPLE 9

A fluorine-containing polymer according to Example 9 was produced as in Example 8, except that the raw material composition C was used instead of the raw material composition A. Then, the weight average molecular weight of the fluorine-containing polymer according to Example 9 was measured, and the relative standard deviation was calculated, which is the numerical value obtained by dividing the standard deviation of the weight average molecular weight of the fluorine-containing polymer by the average weight average molecular weight of the fluorine-containing polymer. Table 2 shows the results.

COMPARATIVE EXAMPLE 1

A fluorine-containing polymer according to Comparative Example 1 was produced as in Example 1, except that the raw material composition F was used instead of the raw material composition A. Then, the weight average molecular weight of the fluorine-containing polymer according to Comparative Example 1 was measured, and the relative standard deviation was calculated, which is the numerical value obtained by dividing the standard deviation of the weight average molecular weight of the fluorine-containing polymer by the average weight average molecular weight of the fluorine-containing polymer. Table 2 shows the results.

COMPARATIVE EXAMPLE 2

A fluorine-containing polymer according to Comparative Example 2 was produced as in Example 8, except that the raw material composition F was used instead of the raw material composition A. Then, the weight average molecular weight of the fluorine-containing polymer according to Comparative Example 2 was measured, and the relative standard deviation was calculated, which is the numerical value obtained by dividing the standard deviation of the weight average molecular weight of the fluorine-containing polymer by the average weight average molecular weight of the fluorine-containing polymer. Table 2 shows the results.

As shown in Table 2, the RSD values of the fluorine-containing polymers according to Examples 1 to 9 produced from the raw material compositions having a concentration of 1,1,1-trifluoro-2-(trifluoromethyl)pentane-2,4-diyl methacrylate (the fluorine-containing monomer of formula (5-1)) of 1500 ppm or less were small.

In contrast, the RSD values of the fluorine-containing polymers according to Comparative Examples 1 and 2 produced from the raw material composition F having a concentration of 1,1,1-trifluoro-2-(trifluoromethyl)pentane-2,4-diyl methacrylate (the fluorine-containing monomer of formula (5-1)) of more than 1500 ppm were large.

The invention claimed is:

1. A method for producing a fluorine-containing polymer containing a repeating unit represented by the following formula (1) and a repeating unit represented by the following formula (2), the method comprising:

a step for synthesizing a fluorine-containing monomer, the step comprising: reacting a diol represented by the following formula (3) with at least one selected from the group consisting of unsaturated carboxylic acids, esters of the unsaturated carboxylic acids, acid halides of the unsaturated carboxylic acids, and anhydrides of the unsaturated carboxylic acids, to obtain a composition containing a fluorine-containing monomer represented by the following formula (4) as a main reaction product and a fluorine-containing monomer represented by the following formula (5) as a minor reaction product;

a step for purifying the obtained composition containing the fluorine-containing monomer, the step comprising: removing the fluorine-containing monomer of formula (5) from the composition to adjust an amount of the fluorine-containing monomer of formula (5), expressed in parts per million based on a mass of the fluorine-containing monomer of formula (4), to 500 ppm or less; and a polymerization step, the step comprising: performing a polymerization reaction of the composition obtained after the fluorine-containing monomer purification to give a fluorine-containing polymer containing a repeating unit of formula (1) and a repeating unit of formula (2),

TABLE 2

| | | Weight average molecular weight | | | | | | | |
|---|---|---|---|---|---|---|---|---|---|
| | Composition | N = 1 | N = 2 | N = 3 | N = 4 | N = 5 | N = 6 | Average | RSD |
| Example 1 | Raw material composition A | 9575 | 9616 | 9587 | 9578 | 9607 | 9585 | 9591 | 0.17 |
| Example 2 | Raw material composition B | 9581 | 9585 | 9619 | 9617 | 9628 | 9598 | 9605 | 0.20 |
| Example 3 | Raw material composition C | 9592 | 9630 | 9647 | 9571 | 9621 | 9565 | 9604 | 0.35 |
| Example 4 | Raw material composition D | 9516 | 9547 | 9617 | 9671 | 9667 | 9705 | 9621 | 0.78 |
| Example 5 | Raw material composition E | 9545 | 9603 | 9622 | 9769 | 9558 | 9462 | 9593 | 1.07 |
| Example 6 | Raw material composition A + monomer of formula (11) | 9669 | 9652 | 9639 | 9671 | 9622 | 9667 | 9653 | 0.20 |
| Example 7 | Raw material composition C + monomer of formula (11) | 9684 | 9705 | 9644 | 9603 | 9636 | 9619 | 9649 | 0.40 |
| Example 8 | Raw material composition A + monomer of formula (12) | 9532 | 9537 | 9544 | 9567 | 9534 | 9554 | 9545 | 0.14 |
| Example 9 | Raw material composition C + monomer of formula (12) | 9503 | 9509 | 9590 | 9545 | 9541 | 9562 | 9542 | 0.34 |
| Comparative Example 1 | Raw material composition F | 9780 | 9455 | 9507 | 9703 | 9614 | 9681 | 9623 | 1.28 |
| Comparative Example 2 | Raw material composition F + monomer of formula (12) | 9559 | 9591 | 9679 | 9747 | 9711 | 9383 | 9612 | 1.38 |

(1)

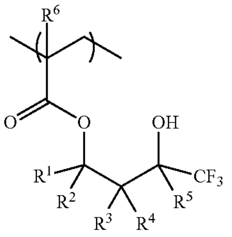

(2)

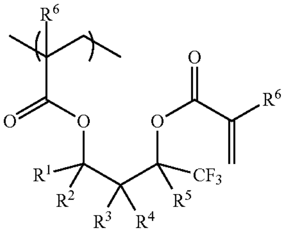

(3)

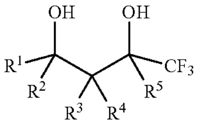

(4)

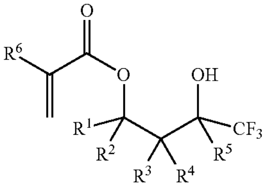

(5)

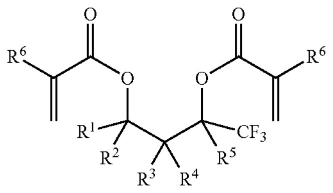

wherein $R^1$ and $R^2$ are each independently a hydrogen atom, a methyl group, an ethyl group, an n-propyl group, an iso-propyl group, an n-butyl group, an iso-butyl group, a sec-butyl group, or a t-butyl group; $R^3$ and $R^4$ are each independently a hydrogen atom, a methyl group, or an ethyl group; $R^5$ is a hydrogen atom or a trifluoromethyl group; and $R^6$ is a hydrogen atom, a chlorine atom, a methyl group, or a trifluoromethyl group.

2. The method for producing a fluorine-containing polymer according to claim 1, wherein in the polymerization step, the fluorine-containing polymer is synthesized such that a relative standard deviation, which is a numerical value obtained by dividing a standard deviation of a weight average molecular weight of the fluorine-containing polymer to be obtained by an average weight average molecular weight of the fluorine-containing polymer, is 0.10 to 1.10.

3. The method for producing a fluorine-containing polymer according to claim 1, wherein $R^5$ is a trifluoromethyl group.

4. The method for producing a fluorine-containing polymer according to claim 1, wherein $R^3$ and $R^4$ are hydrogen atoms.

5. The method for producing a fluorine-containing polymer according to claim 1, wherein $R^1$ is a methyl group or an iso-propyl group, and $R^2$ is a hydrogen atom.

6. The method for producing a fluorine-containing polymer according to claim 1, wherein the polymerization step includes performing the polymerization reaction of the composition containing another monomer other than the fluorine-containing monomer of formula (4) and the fluorine-containing monomer of formula (5).

7. The method for producing a fluorine-containing polymer according to claim 1, wherein the polymerization reaction in the polymerization step is a radical polymerization reaction.

8. The method for producing a fluorine-containing polymer according to claim 7, wherein the radical polymerization reaction is performed in an organic solvent.

9. A composition, comprising:

a fluorine-containing monomer represented by the following formula (4); and a fluorine-containing monomer represented by the following formula (5) in an amount, expressed in parts per million based on a mass of the fluorine-containing monomer of formula (4), of 500 ppm or less, (4)

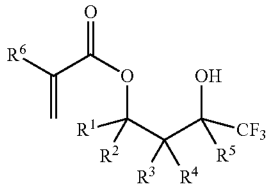

(5)

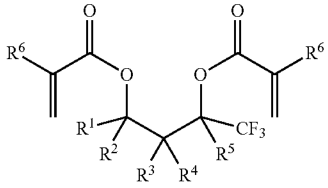

wherein $R^1$ and $R^2$ are each independently a hydrogen atom, a methyl group, an ethyl group, an n-propyl group, an iso-propyl group, an n-butyl group, an iso-butyl group, a sec-butyl group, or a t-butyl group; $R^3$ and $R^4$ are each independently a hydrogen atom, a methyl group, or an ethyl group; $R^5$ is a hydrogen atom or a trifluoromethyl group; and $R^6$ is a hydrogen atom, a chlorine atom, a methyl group, or a trifluoromethyl group.

10. The composition according to claim 9, wherein $R^5$ is a trifluoromethyl group.

11. The composition according to claim 9, wherein $R^3$ and $R^4$ are hydrogen atoms.

12. The composition according to claim 9, wherein $R^1$ is a methyl group or an iso-propyl group, and $R^2$ is a hydrogen atom.

13. The composition according to claim 9, further comprising another monomer other than the fluorine-containing monomer of formula (4) and the fluorine-containing monomer of formula (5).

14. The composition according to claim 9, further comprising an organic solvent.

15. The method for producing a fluorine-containing polymer according to claim 1, wherein the at least one selected from the group consisting of unsaturated carboxylic acids, esters of the unsaturated carboxylic acids, acid halides of the unsaturated carboxylic acids, and anhydrides of the unsaturated carboxylic acids in the synthesis step is selected from methacrylating agents, acrylating agents, or other esterifying agents.

16. The method for producing a fluorine-containing polymer according to claim 1, wherein in the synthesis step, the reaction of the diol represented by the formula (3) with at least one selected from the group consisting of unsaturated carboxylic acids, esters of the unsaturated carboxylic acids, acid halides of the unsaturated carboxylic acids, and anhydrides of the unsaturated carboxylic acids is performed in the presence of an organic solvent.

17. The method for producing a fluorine-containing polymer according to claim 16, wherein the organic solvent is hexane, heptane, toluene, or ethyl acetate.

* * * * *